(12) United States Patent
Enomura

(10) Patent No.: US 9,242,922 B2
(45) Date of Patent: Jan. 26, 2016

(54) METHOD FOR PRODUCING BARIUM TITANYL SALT AND BARIUM TITANATE

(75) Inventor: Masakazu Enomura, Izumi (JP)

(73) Assignee: M. TECHNIQUE CO., LTD., Izumi-Shi, Osaka (JP)

( * ) Notice: Subject to any disclaimer, the term of this patent is extended or adjusted under 35 U.S.C. 154(b) by 246 days.

(21) Appl. No.: 14/009,015

(22) PCT Filed: Mar. 27, 2012

(86) PCT No.: PCT/JP2012/057912
§ 371 (c)(1),
(2), (4) Date: Sep. 30, 2013

(87) PCT Pub. No.: WO2012/137628
PCT Pub. Date: Oct. 11, 2012

(65) Prior Publication Data
US 2014/0221685 A1    Aug. 7, 2014

(30) Foreign Application Priority Data

Apr. 1, 2011   (JP) .................................. 2011-082003

(51) Int. Cl.
| | | |
|---|---|---|
| *C07C 51/42* | (2006.01) | |
| *C01G 23/02* | (2006.01) | |
| *C04B 35/468* | (2006.01) | |
| *C07C 51/41* | (2006.01) | |
| *C01G 23/00* | (2006.01) | |

(52) U.S. Cl.
CPC ............ *C07C 51/412* (2013.01); *C01G 23/006* (2013.01); *C04B 35/4682* (2013.01); *C01P 2002/72* (2013.01); *C01P 2004/04* (2013.01); *C04B 2235/449* (2013.01)

(58) Field of Classification Search
CPC .. C07C 51/412; C01G 23/006; C01P 2004/04
See application file for complete search history.

(56) References Cited

U.S. PATENT DOCUMENTS

| 2002/0048547 A1* | 4/2002 | Lee et al. ....................... 423/598 |
|---|---|---|
| 2010/0215958 A1 | 8/2010 | Enomura |
| 2011/0015054 A1 | 1/2011 | Enomura |
| 2011/0042626 A1* | 2/2011 | Enomura ....................... 252/514 |

FOREIGN PATENT DOCUMENTS

| CN | 1295976 A | | 5/2001 |
|---|---|---|---|
| CN | 1699179 A | | 11/2005 |
| CN | 1800099 A | | 7/2006 |
| CN | 1865153 A | | 11/2006 |
| CN | 101333000 A | | 12/2008 |
| CN | 101333000 B | * | 12/2008 |
| CN | 101795772 A | | 8/2010 |
| CN | 101808942 A | | 8/2010 |
| CN | 101855713 A | | 10/2010 |
| EP | 2 184 109 A1 | | 5/2010 |
| JP | 2004-123431 A | | 4/2004 |
| JP | 2006-321722 A | | 11/2006 |
| JP | 2006-321723 A | | 11/2006 |
| JP | 2009-131831 A | | 6/2009 |
| JP | 2010-173932 A | | 8/2010 |
| RU | 2 253 616 C1 | | 6/2005 |
| WO | WO 2009/008392 A1 | | 1/2009 |
| WO | WO 2009/008393 A1 | | 1/2009 |
| WO | WO 2009/035019 A1 | | 3/2009 |
| WO | WO 2009/038008 A1 | | 3/2009 |

OTHER PUBLICATIONS

Zaragoza Dorwald (Side Reactions in Organic Synthesis, 2005, WILEY-VCH Verlag GmbH & Co. KGaA, Weinheim, Preface. p. IX.*
Hursthouse et al, Organic Process Research & Development, Why Do Organic Compounds Crystallise Well or Badly or Ever so Slowly? Why Is Crystallisation Nevertheless Such a Good Purification Technique?, 2009, 13, pp. 1231-1240.*

* cited by examiner

*Primary Examiner* — Paul A Zucker
(74) *Attorney, Agent, or Firm* — Birch, Stewart, Kolasch & Birch, LLP

(57) ABSTRACT

A method for producing a high-quality barium titanyl salt includes using, as the fluids to be treated, at least two kinds of fluids, namely, a barium titanium mixed solution that is obtained by dissolving both a barium compound and a titanium compound in a solvent, a compound solution that is obtained by dissolving, in a solvent, a compound capable of deposing the barium and titanium contained in the barium-titanium mixed solution into a barium titanyl salt, and if necessary, one or more other fluids; and mixing these fluids together in a thin film fluid formed at least between two treating surfaces and to form a barium titanyl salt. The treating surfaces are so arranged as to face each other in an approachable/separable state with one of the treating surfaces and being capable of turning relatively to the other.

11 Claims, 5 Drawing Sheets

(A)

(B)

METHOD FOR PRODUCING BARIUM TITANYL SALT AND BARIUM TITANATE

The present invention relates to a method for producing barium titanyl salt and barium titanate.

BACKGROUND ART

A barium titanyl salt represented by barium titanyl oxalate is used as a raw material for barium titanate used mainly for a piezoelectric material, a semiconductor material, a dielectric material, a laminated ceramic condenser material, a sensor, and so on. In the barium titanate for these uses, it is required that this be microparticles and that the ratio of barium (Ba) to titanium (Ti) contained the barium titanate (mol ratio) be kept uniform (Ba/Ti is about 1).

As to the method for producing barium titanate, there may be mentioned, for example, a solid phase method typically represented by the method in which barium titanate is obtained by heat treatment of a powder mixture of titanium oxide and barium carbonate, a hydrothermal synthesis method as described in Patent Document 1, and a sol-gel method in which hydrolysis of alkoxides of barium and of titanium is used. However, from view of the production cost and energy, a method in which barium titanate is synthesized by heat treatment of the foregoing barium titanyl salt is general, wherein the oxalate method in which barium titanyl oxalate (barium titanyl oxalate salt) is used as the barium titanyl salt as shown in Patent Document 2 is the most general from view of the production cost and availability of the raw materials thereof.

Generally, however, in the case when barium titanate microparticle is synthesized by the oxalate method, because barium titanyl oxalate, which is a precursor to barium titanate, is in the form of coarse particles, a pulverization process is necessary to change it to microparticles; as a result, in many cases, the barium titanyl oxalate microparticle thus obtained hardly shows crystallinity. The barium titanate obtained by burning the barium titanyl oxalate like this readily becomes a coarse barium titanate again, and on top of it the ratio between the barium and the titanium contained therein becomes uneven or inhomogeneous in entirety of the barium titanate powders in a certain instance.

Applicant of the present invention provided a method for producing microparticles, wherein microparticles are separated in a thin film fluid running between processing surfaces which are disposed in a position they are faced with each other, as shown in Patent Document 3; but a method for producing the barium titanyl salt having a controlled ratio between the barium and the titanium had not been disclosed specifically.

PRIOR ART DOCUMENTS

Patent Document

Patent Document 1: Japanese Patent Laid-Open Publication No. 2010-173932
Patent Document 2: Japanese Patent Laid-Open Publication No. 2004-123431
Patent Document 3: International Patent Laid-Open Publication No. 2009/008393

DISCLOSURE OF THE INVENTION

Problems to be Solved by the Invention

The present invention was made to solve the problems mentioned above; and the object thereof is to provide a method for producing an excellent barium titanyl salt. Preferably, the present invention intends to provide a method for producing microparticles of a barium titanyl salt having not only crystallinity but also a controlled ratio between the barium and the titanium.

Means for Solving the Problems

Inventor of the present invention carried out an extensive investigation, and as a result, during the time to separate a barium titanyl salt by mixing—as the fluids to be processed, namely, a barium-titanium mixed solution in which a barium compound and a titanium compound are dissolved, a compound solution to separate the barium and the titanium contained in the barium-titanium mixed solution as the barium titanyl salt, and optionally a fluid which contains a third solvent—, between at least two processing surfaces which are disposed in a position they are faced with each other so as to be able to approach to and separate from each other, at least one of which rotates relative to the other, they found that, if at least one kind of an acidic substance is contained in the barium-titanium mixed solution and/or the compound solution and/or the third solvent, the barium titanyl salt having the ratio of barium to titanium controlled at about 1 can be obtained; and based on this finding, the present invention could be completed.

The invention according to claim 1 of the present application provides a method for producing a barium titanyl salt: using at least two fluids as fluids to be processed, of these fluids, at least one fluid is a barium-titanium mixed solution in which a barium compound and a titanium compound are dissolved in a solvent, and at least one fluid other than the said fluid is a compound solution in which at least one compound to separate, as the barium titanyl salt, the barium and the titanium which are contained in the barium-titanium mixed solution is dissolved in a solvent, whereby the said two or more of the fluids to be processed are mixed to separate the barium titanyl salt, wherein at least one acidic substance is contained in at least any one of the barium-titanium mixed solution, the compound solution, and at least one solvent different from the barium-titanium mixed solution and the compound solution, the said two, or three or more of the fluids to be processed are mixed in a thin film fluid formed between at least two processing surfaces which are disposed in a position they are faced with each other so as to be able to approach to and separate from each other, at least one of which rotates relative to the other, thereby separating the barium titanyl salt.

The invention according to claim 2 of the present application provides a method for producing a barium titanyl salt: using at least three fluids as fluids to be processed, of these fluids, at least one fluid is a barium solution in which a barium compound is dissolved in a solvent, at least one fluid other than the said fluid is a titanium solution in which a titanium compound is dissolved in a solvent, and at least one fluid other than these fluids is a compound solution in which at least one compound is dissolved in a solvent, the said compound being to separate, as the barium titanyl salt, the barium which is contained in the barium solution and the titanium which is contained in the titanium solution, whereby the said three or more fluids to be processed are mixed to separate the barium titanyl salt, wherein at least one acidic substance is contained in at least any one of the barium solution, the titanium solution, the compound solution, and at least one solvent different from the barium solution, the titanium solution, and the compound solution, the said three, or four or more of the fluids to be processed are mixed in a thin film fluid formed between at least two processing surfaces which are disposed in a position they are faced with each other so as to be able to approach to and separate from each other, at least one of which rotates relative to the other, thereby separating the barium titanyl salt.

The invention according to claim 3 of the present application provides the method for producing a barium titanyl salt according to claim 1 or 2, wherein the barium titanyl salt is crystalline.

The invention according to claim 4 of the present application provides the method for producing a barium titanyl salt according to any of claims 1 to 3, wherein the compound is oxalic acid and/or a metal salt of oxalic acid, and the barium titanyl salt to be obtained is barium titanyl oxalate.

The invention according to claim 5 of the present application provides a method for producing barium titanate from the barium titanyl salt produced by the method for producing a barium titanyl salt according to any of claims 1 to 4.

According to mere one embodiment of the present invention, the present invention may be carried out as a method for producing a barium titanyl salt, wherein the method comprises:

a fluid pressure imparting mechanism for imparting a pressure to a fluid to be processed, a first processing member provided with a first processing surface of the at least two processing surfaces, a second processing member provided with a second processing surface of the at least two processing surfaces, and a rotation drive mechanism for rotating these processing members relative to each other; wherein each of the processing surfaces constitutes part of a sealed flow path through which the fluid to be processed under the pressure is passed, of the first and the second processing members, at least the second processing member is provided with a pressure-receiving surface, and at least part of this pressure-receiving surface is comprised of the second processing surface, the pressure-receiving surface receives a pressure applied to the fluid to be processed by the fluid pressure imparting mechanism thereby generating a force to move in the direction of separating the second processing surface from the first processing surface, the fluid to be processed under the pressure is passed between the first processing surface and the second processing surface which are disposed in a position they are faced with each other so as to be able to approach to and separate from each other, at least one of which rotates relative to the other, whereby the fluid to be processed forms a thin film fluid, and a barium titanyl salt is separated in this thin film fluid.

According to mere another embodiment of the present invention, the present invention may be carried out as a method for producing a barium titanyl salt, wherein at least one fluid of the fluids to be processed passes through between both the processing surfaces while forming the thin film fluid, an another introduction path independent of the flow path for the foregoing at least one fluid is provided, at least one opening leading to this introduction path is arranged in at least any one of the first processing surface and the second processing surface, at least one fluid which is different from the foregoing at least one fluid is introduced into between the processing surfaces through this opening, the fluids to be processed are mixed in the thin film fluid, and a barium titanyl salt is separated in this thin film fluid.

In addition, according to a mere one embodiment of the present invention, this method can be executed as the method for producing a barium titanyl salt, wherein of the fluids to be processed, at least any one of the fluids passes through between the processing surfaces while forming the thin film fluid, at least two separate introduction paths independent of a flow path through which the at least any one of the fluids to be processed passes is arranged, the at least two separate introduction paths are independent with each other, at least any one of the first processing surface and the second processing surface is provided with separate openings respectively for the at least two separate introduction paths, the fluid to be processed other than the at least any one of the fluids is introduced into between the processing surfaces through the separate openings, whereby mixing the fluids to be processed in the thin film fluid, thereby separating the barium titanyl salt in this thin film fluid.

Advantages

According to the present invention, the barium titanyl salt having the ratio of barium to titanium controlled at about 1 can be obtained more conveniently with lower energy and cost than ever, so that the barium titanyl salt especially suitable as a raw material for barium titanate can be provided cheaply and stably. In addition, the barium titanyl salt can be produced easily as microparticles, so that microparticles of the barium titanyl salt in accordance with the purpose can be provided.

BRIEF DESCRIPTION OF DRAWINGS

FIG. 1 is a schematic sectional view showing the fluid processing apparatus according to an embodiment of the present invention.
FIG. 2(A) is a schematic plane view of the first processing surface in the fluid processing apparatus shown in FIG. 1,
and FIG. 2(B) is an enlarged view showing an important part of the processing surface in the apparatus.
FIG. 3(A) is a sectional view of the second introduction member of the apparatus,
and FIG. 3(B) is an enlarged view showing an important part of the processing surface for explaining the second introduction member.

MODES FOR CARRYING OUT THE INVENTION

Figure 1:
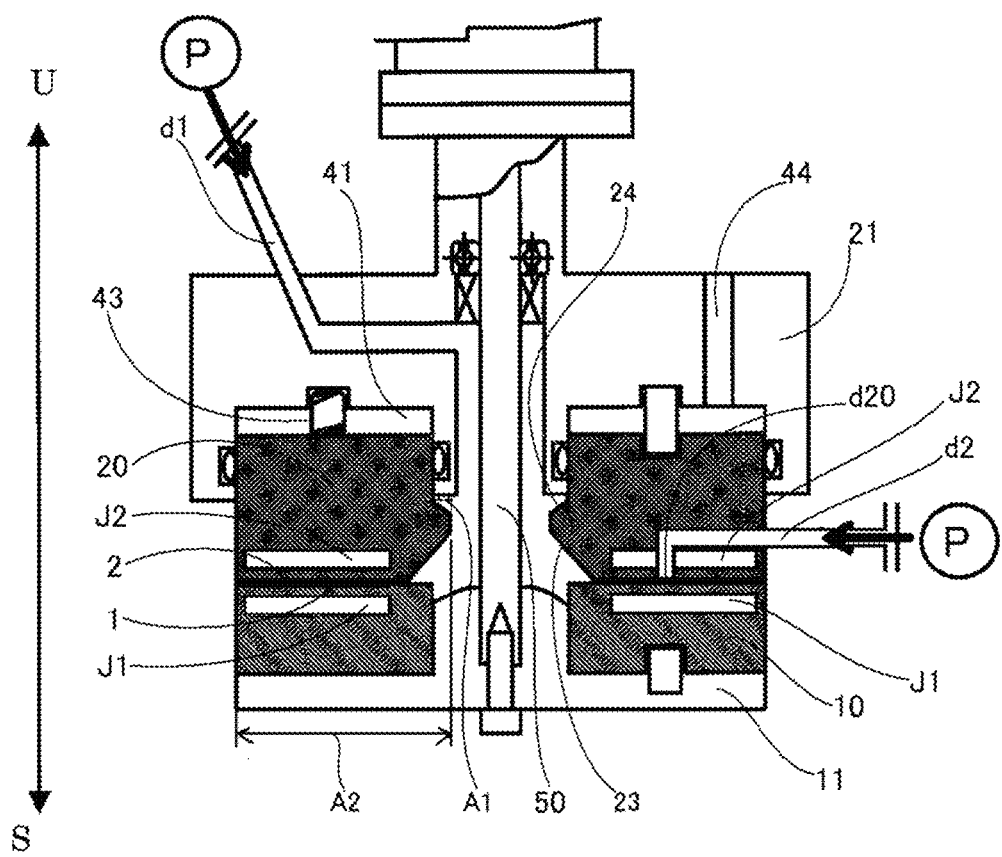
[FIG. 1]

Hereinafter, the present invention will be explained in detail. However, the technical scope of the present invention is not restricted by the following embodiments nor Examples.

Illustrative example of the compound to produce the barium titanyl salt of the present invention includes oxalic acid, succinic acid, citric acid, and a metal salt of them (Na salt, K salt, and so forth); however, in view of the production cost thereof, oxalic acid and/or a metal salt of oxalic acid are preferable. These compounds each may be used solely or as a mixture of plurality of two or more of them.

There is no particular restriction as to the barium compound and the titanium compound to produce the barium titanyl salt; and illustrative example thereof includes a metal of a barium and of a titanium (single body); a barium and a titanium in the form of respective salts such as a nitrate salt, a nitrite salt, a sulfate salt, a sulfite salt, a formate salt, an acetate salt, a phosphate salt, a phosphite salt, a hypophosphite salt, a chloride, an oxy salt, and an acetylacetonato salt; a barium and a titanium in the form of a hydroxide, an oxide, and a hydroxylated oxide; and an organic compound such as a barium alkoxide and a titanium alkoxide. These compounds each may be used solely or as a mixture of plurality of two or more of them.

Illustrative example of the barium titanyl salt of the present invention includes barium titanyl oxalate, barium titanyl succinate, and barium titanyl citrate; but, in the present invention, in view of the production cost, barium titanyl oxalate is preferable. The ratio of the barium to the titanium (mol ratio) contained in the barium titanyl salt of the present invention is about 1, or preferably in the range of 0.9 to 1.1. In addition, if the titanium compound is replaced with a zirconium compound and the barium compound is replaced with a compound of strontium, calcium, magnesium, lead, or zinc, strontium titanate, zinc titanate, barium zirconate, magnesium zirconate, or the like may be easily produced by the present invention.

Alternatively, the barium titanyl salt may be made to contain a minute amount of an element as a dope element. There is no particular restriction in the dope element, so that all elements in the periodic table may be mentioned; however, in the case that preparation of the barium titanate for the use as a dielectric material is intended, preferable element thereof includes alkaline earth metals such as strontium and calcium, rare earth metals such as yttrium, neodymium, samarium, and dysprosium; and zinc. In these dope elements also, similarly to the barium compounds and the titanium compounds, the dope elements as a single body as well as in the form of a salt, an organic compound, and so forth may be used.

Illustrative example of the solvent to dissolve the compound, the barium compound, the titanium compound, and optionally the dope element or a compound containing the dope element includes water, an organic solvent, and a mixed solvent comprising a plurality of them. Illustrative example of the water includes a tap water, an ion-exchanged water, a purified water, a ultrapurified water, and a RO water; and illustrative example of the organic solvent includes an alcohol compound solvent, an amide compound solvent, a ketone compound solvent, an ether compound solvent, an aromatic compound solvent, carbon disulfide, an aliphatic compound solvent, a nitrile compound solvent, a sulfoxid compound solvent, a halogen compound solvent, an ester compound solvent, anionic liquid, a carboxylic acid compound, and a sulfonic acid compound. These solvents each may be used solely or as a mixture of two or more of them.

Alternatively, a basic substance or an acidic substance may be used by mixing it with or dissolving it into the forgoing solvents so far as this embodiment does not cause an adverse effect to separation of the barium titanyl salt. Illustrative example of the basic substance includes metal hydroxides such as sodium hydroxide and potassium hydroxide, metal alkoxides such as sodium methoxide and sodium isopropoxide, and amine compounds such as triethylamine, 2-diethylaminoethanol, and diethylamine. Illustrative example of the acidic substance includes inorganic acids such as aqua regia, hydrochloric acid, nitric acid, fuming nitric acid, sulfuric acid, and fuming sulfuric acid; and organic acids such as formic acid, acetic acid, chloroacetic acid, dichloroacetic acid, oxalic acid, trifluoroacetic acid, and trichloroacetic acid. These basic substances or acidic substances may be respectively used solely or as a mixture with the solvents mentioned before.

To explain the above solvents in more detail, illustrative example of the alcohol compound solvent includes linear alcohols such as methanol, ethanol, n-butanol, and n-propanol; branched alcohols such as isopropanol, 2-butanol, and tert-butanol; and polyalcohols such as ethylene glycol and diethylene glycol. Illustrative example of the ketone compound solvent includes acetone, methyl ethyl ketone, and cyclohexanone. Illustrative example of the ether compound solvent includes dimethyl ether, diethyl ether, tetrahydrofurane, and propylene glycol monomethyl ether. Illustrative example of the aromatic compound solvent includes nitrobenzene, chlorobenzene, and dichlorobenzene. Illustrative example of the aliphatic compound solvent includes hexane. Illustrative example of the nitrile compound solvent includes acetonitrile. Illustrative example of the sulfoxide compound solvent includes dimethyl sulfoxide, diethyl sulfoxide, hexamethylenesulfoxide, and sulfolane. Illustrative example of the halogen compound solvent includes chloroform, dichloromethane, trichloroethylene, and iodoform. Illustrative example of the ester compound solvent includes ethyl acetate, butyl acetate, methyl lactate, ethyl lactate, and 2-(1-methoxy)propyl acetate. Illustrative example of the ionic liquid includes a salt between 1-butyl-3-methylimidazolium and $PF6^-$ (hexafluorophosphate ion). Illustrative example of the amide compound solvent includes N,N-dimethylformamide, 1-methyl-2-pyrrolidone, 2-pyrrolidinone, 1,3-dimethyl-2-imidazolidinone, 2-pyrrolidinone, epsilon-caprolactam, formamide, N-methylformamide, acetamide, N-methylacetamide, N,N-dimetnylacetamide, N-methylpropanamide, and hexamethylphosphoric triamide. Illustrative example of the carboxylic acid compound includes 2,2-dichloropropionic acid and squaric acid. Illustrative example of the sulfonic acid compound includes methanesulfonic acid, p-toluenesulfonic acid, chlorosulfonic acid, and trifluoromethanesulfonic acid.

In the present invention, the compound solution, the barium solution, the titanium solution, the barium-titanium mixed solution, and optionally the solution in which a dope element is dissolved in a solvent are prepared by using the compound, the barium compound, the titanium compound, and optionally the dope element or a compound containing the dope element, and the solvent. Among them, mixing of the titanium solution with the compound solution is not preferable because there is a possibility of separating an insoluble titanium salt or the like depending on the order of the mixing and the like; however, this may be allowed so far as the adverse effect by this mixing is to the degree not to make execution of the present invention impossible.

In the present invention, it is possible to obtain about 1 as the ratio of the barium to the titanium (mol ratio) contained in the barium titanyl salt to be separated by making at least any one of the barium-titanium mixed solution and the compound solution to contain an acidic substance during the time of separating the barium titanyl salt by mixing the barium-titanium mixed solution with the compound solution. In addition, in the present invention, it is possible to obtain about 1 as the ratio of the barium to the titanium (mol ratio) contained in the barium titanyl salt to be separated by making at least any one of the barium solution, the titanium solution, and the compound solution to contain an acidic substance during the time of separating the barium titanyl salt by mixing the barium solution, the titanium solution, and the compound solution. Further in addition, in the present invention, it is possible to obtain about 1 as the ratio of the barium to the titanium (mol ratio) contained in the barium titanyl salt to be separated even in the case that all of the fluid containing the acidic substance, the barium-titanium mixed solution (or the barium solution and the titanium solution), and the compound solution are mixed by using the respective separate independent flow paths (this will be discussed later) just before the treatment to separate the barium titanyl salt during the time of separating the barium titanyl salt by mixing the barium-titanium mixed solution (or the barium solution and the titanium solution) with the compound solution. There is no particular restriction as to the acidic substance in the present invention, and the same acid as mentioned before may be used, while nitric acid, sulfuric acid, and hydrochloric acid may be preferably used; though nitric acid is especially preferable. In the present invention, the barium-titanium mixed solution, the barium solution, the titanium solution, the compound solution, and the reaction solution containing the barium titanyl salt which is separated by mixing the barium-titanium mixed solution (or the barium solution and the titanium solution) with the compound solution are preferably acidic, more preferably pH of less than 3, or still more preferably pH of less than 1.

In the present invention, mixing of the barium-titanium mixed solution (or the barium solution and the titanium solution) with the compound solution is done preferably by a method wherein the mixing and stirring is executed uniformly in the thin film fluid formed between the processing surfaces which are disposed in a position they are faced with each other so as to be able to approach to and separate from each other, at least one of which rotates relative to the other. As to the apparatus like this, for example, the apparatus based on the same principle as the one described in the Patent Document 3 which was filed by the present Applicant may be used. By using the apparatus based on the principle shown there, microparticles of the barium titanyl salt can be produced uniformly and homogeneously.

Hereinafter, embodiments of the above-mentioned apparatus will be explained by using the drawings.

Figure 2:
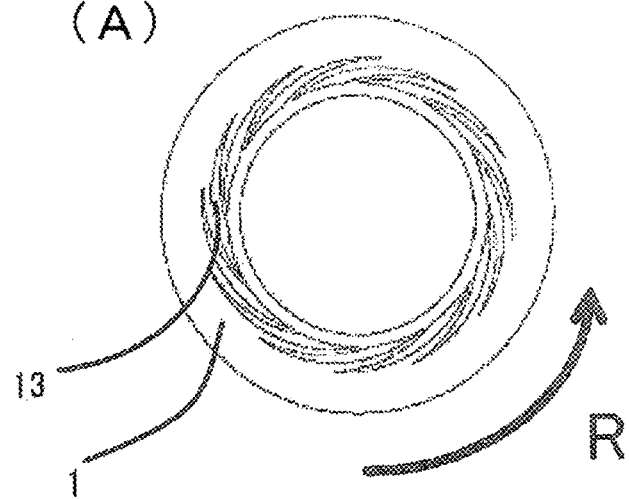
[FIG. 2]
Figure 2:
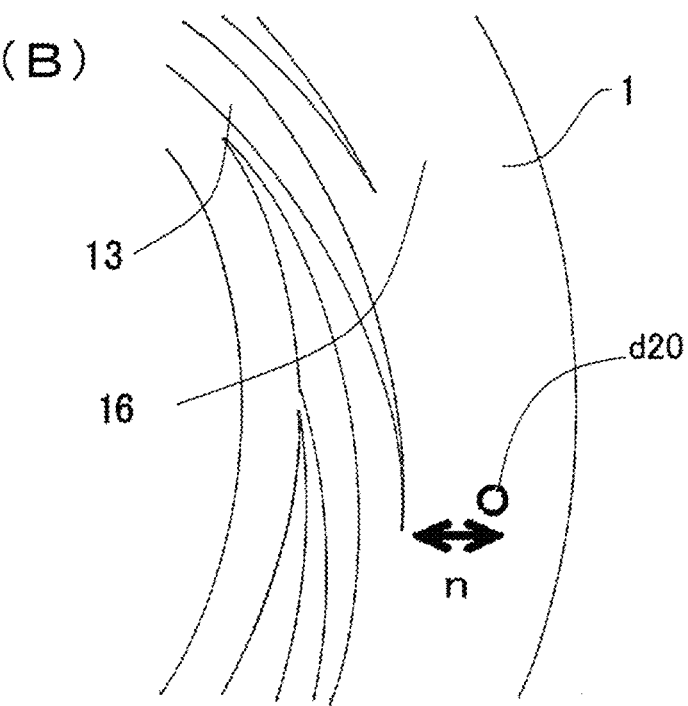
Figure 3:
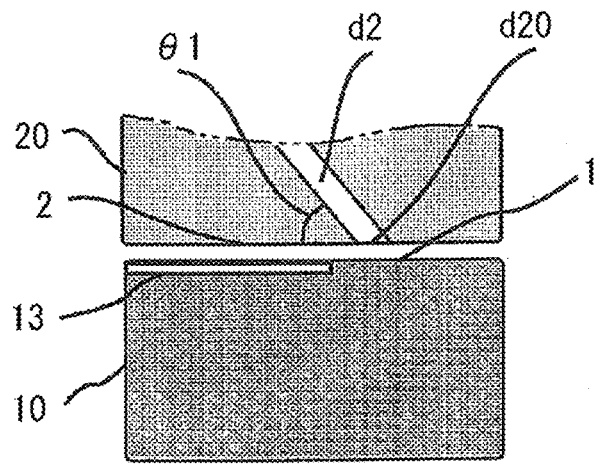
[FIG. 3]
Figure 3:
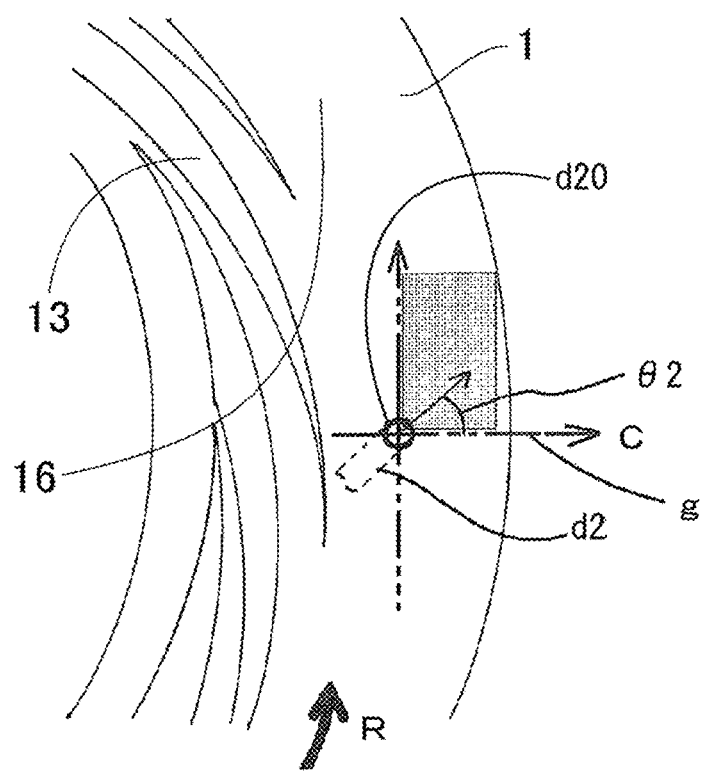

The fluid processing apparatus shown in FIG. 1 to FIG. 3 is similar to the apparatus described in Patent Document 3, with which a material to be processed is processed between processing surfaces in processing members arranged so as to be able to approach to and separate from each other, at least one of which rotates relative to the other; wherein, of the fluids to be processed, a first fluid to be processed, i.e., a first fluid, is introduced into between the processing surfaces, and a second fluid to be processed, i.e., a second fluid, is introduced into between the processing surfaces from a separate path that is independent of the flow path introducing the fluid and has an opening leading to between the processing surfaces, whereby the first fluid and the second fluid are mixed and stirred between the processing surfaces. Meanwhile, in FIG. 1, a reference character U indicates an upside and a reference character S indicates a downside; however, up and down, front and back and right and left shown therein indicate merely a relative positional relationship and does not indicate an absolute position. In FIG. 2(A) and FIG. 3(B), reference character R indicates a rotational direction. In FIG. 3(C), reference character C indicates a direction of centrifugal force (a radial direction).

In this apparatus provided with processing surfaces arranged opposite to each other so as to be able to approach to and separate from each other, at least one of which rotates relative to the other, at least two kinds of fluids as fluids to be processed are used, wherein at least one fluid thereof contains at least one kind of material to be processed, a thin film fluid is formed by converging the respective fluids between these processing surfaces, and the material to be processed is processed in this thin film fluid. With this apparatus, a plurality of fluids to be processed may be processed as mentioned above; but a single fluid to be processed may be processed as well.

This fluid processing apparatus is provided with two processing members of a first processing member 10 and a second processing member 20 arranged opposite to each other, wherein at least one of these processing members rotates. The surfaces arranged opposite to each other of the respective processing members 10 and 20 are made to be the respective processing surfaces. The first processing member 10 is provided with a first processing surface 1 and the second processing member 20 is provided with a second processing surface 2.

The processing surfaces 1 and 2 are connected to a flow path of the fluid to be processed and constitute part of the flow path of the fluid to be processed. Distance between these processing surfaces 1 and 2 can be changed as appropriate; and thus, the distance thereof is controlled so as to form a minute space usually in the range of 1 mm or less, for example, 0.1 μm to 50 μm. With this, the fluid to be processed passing through between the processing surfaces 1 and 2 becomes a forced thin film fluid forced by the processing surfaces 1 and 2.

When a plurality of fluids to be processed are processed by using this apparatus, the apparatus is connected to a flow path of the first fluid to be processed whereby forming part of the flow path of the first fluid to be processed; and part of the flow path of the second fluid to be processed other than the first fluid to be processed is formed. In this apparatus, the two paths converge into one, and two fluids to be processed are mixed between the processing surfaces 1 and 2 so that the fluids may be processed by reaction and so on. It is noted here that the term "process(ing)" includes not only the embodiment wherein a material to be processed is reacted but also the embodiment wherein a material to be processed is only mixed or dispersed without accompanying reaction.

To specifically explain, this apparatus is provided with a first holder 11 for holding the first processing member 10, a second holder 21 for holding the second processing member 20, a surface-approaching pressure imparting mechanism, a rotation drive mechanism, a first introduction part d1, a second introduction part d2, and a fluid pressure imparting mechanism p.

As shown in FIG. 2(A), in this embodiment, the first processing member 10 is a circular body, specifically a disk with a ring form. Similarly, the second processing member 20 is a circular disk. Material of the processing members 10 and 20 is not only metal and carbon but also ceramics, sintered metal, abrasion-resistant steel, sapphire, and other metal subjected to hardening treatment, and rigid material subjected to lining, coating, or plating. In the processing members 10 and 20 of this embodiment, at least part of the first and the second surfaces 1 and 2 arranged opposite to each other is mirror-polished.

Roughness of this mirror polished surface is not particularly limited; but surface roughness Ra is preferably 0.01 µm to 1.0 µm, or more preferably 0.03 µm to 0.3 µm.

At least one of the holders can rotate relative to the other holder by a rotation drive mechanism such as an electric motor (not shown in drawings). A reference numeral 50 in FIG. 1 indicates a rotary shaft of the rotation drive mechanism; in this embodiment, the first holder 11 attached to this rotary shaft 50 rotates, and thereby the first processing member 10 attached to this first holder 11 rotates relative to the second processing member 20. As a matter of course, the second processing member 20 may be made to rotate, or the both may be made to rotate. Further in this embodiment, the first and second holders 11 and 21 may be fixed, while the first and second processing members 10 and 20 may be made to rotate relative to the first and second holders 11 and 21.

At least any one of the first processing member 10 and the second processing member 20 is able to approach to and separate from at least any other member, thereby the processing surfaces 1 and 2 are able to approach to and separate from each other.

In this embodiment, the second processing member 20 approaches to and separates from the first processing member 10, wherein the second processing member 20 is accepted in an accepting part 41 arranged in the second holder 21 so as to be able to rise and set. However, as opposed to the above, the first processing member 10 may approach to and separate from the second processing member 20, or both the processing members 10 and 20 may approach to and separate from each other.

This accepting part 41 is a concave portion for mainly accepting that side of the second processing member 20 opposite to the second processing surface 2, and this concave portion is a groove being formed into a circle, i.e., a ring when viewed in a plane. This accepting part 41 accepts the second processing member 20 with sufficient clearance so that the second processing member 20 may rotate. Meanwhile, the second processing member 20 may be arranged so as to be movable only parallel to the axial direction; alternatively, the second processing member 20 may be made movable, by making this clearance larger, relative to the accepting part 41 so as to make the center line of the processing member 20 inclined, namely unparallel, to the axial direction of the accepting part 41, or movable so as to depart the center line of the processing member 20 and the center line of the accepting part 41 toward the radius direction.

It is preferable that the second processing member 20 be accepted by a floating mechanism so as to be movable in the three dimensional direction, as described above.

The fluids to be processed are introduced into between the processing surfaces 1 and 2 from the first introduction part d1 and the second introduction part d2, the flow paths through which the fluids flow, under the state that pressure is applied thereto by a fluid pressure imparting mechanism p consisting of various pumps, potential energy, and so on. In this embodiment, the first introduction part d1 is a path arranged in the center of the circular, second holder 21, and one end thereof is introduced into between the processing surfaces 1 and 2 from inside the circular, processing members 10 and 20. Through the second introduction part d2, the first fluid to be processed and the second fluid to be processed for reaction are introduced into between the processing surfaces 1 and 2. In this embodiment, the second introduction part d2 is a path arranged inside the second processing member 20, and one end thereof is open at the second processing surface 2. The first fluid to be processed which is pressurized with the fluid pressure imparting mechanism p is introduced from the first introduction part d1 to the space inside the processing members 10 and 20 so as to pass through between the first and processing surfaces 1 and 2 to outside the processing members 10 and 20. From the second introduction part d2, the second fluid to be processed which is pressurized with the fluid pressure imparting mechanism p is provided into between the processing surfaces 1 and 2, whereat this fluid is converged with the first fluid to be processed, and there, various fluid processing such as mixing, stirring, emulsification, dispersion, reaction, deposition, crystallization, and separation are effected, and then the fluid thus processed is discharged from the processing surfaces 1 and 2 to outside the processing members 10 and 20. Meanwhile, an environment outside the processing members 10 and 20 may be made negative pressure by a vacuum pump.

The surface-approaching pressure imparting mechanism mentioned above supplies the processing members with force exerting in the direction of approaching the first processing surface 1 and the second processing surface 2 each other. In this embodiment, the surface-approaching pressure imparting mechanism is arranged in the second holder 21 and biases the second processing member 20 toward the first processing member 10.

The surface-approaching pressure imparting mechanism is a mechanism to generate force (hereinafter, surface-approaching pressure) to press the first processing surface 1 of the first processing member 10 and the second processing surface 2 of the second processing member 20 in the direction to make them approach to each other. The mechanism generates a thin film fluid having minute thickness in a level of nanometer or micrometer by the balance between the surface-approaching pressure and the force to separate the processing surfaces 1 and 2 from each other, i.e., the force such as the fluid pressure. In other words, the distance between the processing surfaces 1 and 2 is kept in a predetermined minute distance by the balance between these forces.

In the embodiment shown in FIG. 1, the surface-approaching pressure imparting mechanism is arranged between the accepting part 41 and the second processing member 20. Specifically, the surface-approaching pressure imparting mechanism is composed of a spring 43 to bias the second processing member 20 toward the first processing member 10 and a biasing-fluid introduction part 44 to introduce a biasing fluid such as air and oil, wherein the surface-approaching pressure is provided by the spring 43 and the fluid pressure of the biasing fluid. The surface-approaching pressure may be provided by any one of this spring 43 and the fluid pressure of this biasing fluid; and other forces such as magnetic force and gravitation may also be used. The second processing member 20 recedes from the first processing member 10 thereby making a minute space between the processing surfaces by separating force, caused by viscosity and the pressure of the fluid to be processed applied by the fluid pressure imparting mechanism p, against the bias of this surface-approaching pressure imparting mechanism. By this balance between the surface-approaching pressure and the separating force as mentioned above, the first processing surface 1 and the second processing surface 2 can be set with the precision of a micrometer level; and thus the minute space between the processing surfaces 1 and 2 may be set. The separating force mentioned above includes fluid pressure and viscosity of the fluid to be processed, centrifugal force by rotation of the processing members, negative pressure when negative pressure is applied to the biasing-fluid introduction part 44, and spring force when the spring 43 works as a pulling spring.

This surface-approaching pressure imparting mechanism may be arranged also in the first processing member 10, in place of the second processing member 20, or in both the processing members.

To specifically explain the separation force, the second processing member 20 has the second processing surface 2 and a separation controlling surface 23 which is positioned inside the processing surface 2 (namely at the entering side of the fluid to be processed into between the first and second processing surfaces 1 and 2) and next to the second processing surface 2. In this embodiment, the separation controlling surface 23 is an inclined plane, but may be a horizontal plane. The pressure of the fluid to be processed acts to the separation controlling surface 23 to generate force directing to separate the second processing member 20 from the first processing member 10. Therefore, the second processing surface 2 and the separation controlling surface 23 constitute a pressure receiving surface to generate the separation force.

In the example shown in FIG. 1, an approach controlling surface 24 is formed in the second processing member 20. This approach controlling surface 24 is a plane opposite, in the axial direction, to the separation controlling surface 23 (upper plane in FIG. 1) and, by action of pressure applied to the fluid to be processed, generates force of approaching the second processing member 20 toward the first processing member 10.

Meanwhile, the pressure of the fluid to be processed exerted on the second processing surface 2 and the separation controlling surface 23, i.e., the fluid pressure, is understood as force constituting an opening force in a mechanical seal. The ratio (area ratio A1/A2) of a projected area A1 of the approach controlling surface 24 projected on a virtual plane perpendicular to the direction of approaching and separating the processing surfaces 1 and 2, that is, in the direction of rising and setting of the second processing member 20 (axial direction in FIG. 1), to a total area A2 of the projected area of the second processing surface 2 of the second processing member 20 and the separation controlling surface 23 projected on the virtual plane is called as balance ratio K, which is important for control of the opening force. This opening force can be controlled by the pressure of the fluid to be processed, i.e., the fluid pressure, by changing the balance line, i.e., by changing the area A1 of the approach controlling surface 24.

Sliding surface actual surface pressure P, i.e., the fluid pressure out of the surface-approaching pressures, is calculated according to the following equation:

$$P = P1 \times (K-k) + Ps$$

Here, P1 represents the pressure of a fluid to be processed, i.e., the fluid pressure, K represents the balance ratio, k represents an opening force coefficient, and Ps represents a spring and back pressure.

By controlling this balance line to control the sliding surface actual surface pressure P, the space between the processing surfaces 1 and 2 is formed as a desired minute space, thereby forming a fluid film of the fluid to be processed so as to make the processed substance such as a product fine and to effect uniform processing by reaction.

Meanwhile, the approach controlling surface 24 may have a larger area than the separation controlling surface 23, though this is not shown in the drawing.

The fluid to be processed becomes a forced thin film fluid by the processing surfaces 1 and 2 that keep the minute space therebetween, whereby the fluid is forced to move out from the circular, processing surfaces 1 and 2. However, the first processing member 10 is rotating; and thus, the mixed fluid to be processed does not move linearly from inside the circular, processing surfaces 1 and 2 to outside thereof, but does move spirally from the inside to the outside thereof by a resultant vector acting on the fluid to be processed, the vector being composed of a moving vector toward the radius direction of the circle and a moving vector toward the circumferential direction.

Meanwhile, a rotary shaft 50 is not only limited to be placed vertically, but may also be placed horizontally, or at a slant. This is because the fluid to be processed is processed in a minute space between the processing surfaces 1 and 2 so that the influence of gravity can be substantially eliminated. In addition, this surface-approaching pressure imparting mechanism can function as a buffer mechanism of micro-vibration and rotation alignment by concurrent use of the foregoing floating mechanism with which the second processing member 20 may be held displaceably.

In the first and second processing members 10 and 20, the temperature thereof may be controlled by cooling or heating at least any one of them; in FIG. 1, an embodiment having temperature regulating mechanisms J1 and J2 in the first and second processing members 10 and 20 is shown. Alternatively, the temperature may be regulated by cooling or heating the introducing fluid to be processed. These temperatures may be used to separate the processed substance or may be set so as to generate Benard convection or Marangoni convection in the fluid to be processed between the first and second processing surfaces 1 and 2.

As shown in FIG. 2, in the first processing surface 1 of the first processing member 10, a groove-like depression 13 extended toward an outer side from the central part of the first processing member 10, namely in a radius direction, may be formed. The depression 13 may be, as a plane view, curved or spirally extended on the first processing surface 1 as shown in FIG. 2(B), or, though not shown in the drawing, may be extended straight radially, or bent at a right angle, or jogged; and the concave portion may be continuous, intermittent, or branched. In addition, this depression 13 may be formed also on the second processing surface 2, or on both the first and second processing surfaces 1 and 2. By forming the depression 13 as mentioned above, the micro-pump effect can be obtained so that the fluid to be processed may be sucked into between the first and second processing surfaces 1 and 2.

It is preferable that the base edge of this depression 13 reach the inner periphery of the first processing member 10. The front edge of the depression 13 is extended to the direction of the outer periphery of the first processing surface 1; the depth thereof (cross section area) is made gradually shallower (smaller) from the base edge to the front edge.

Between the front edge of the depression 13 and the outer peripheral of the first processing surface 1 is formed the flat plane 16 not having the depression 13.

When an opening d20 of the second introduction part d2 is arranged in the second processing surface 2, the arrangement is done preferably at a position opposite to the flat surface 16 of the first processing surface 1 arranged at a position opposite thereto.

This opening d20 is arranged preferably in the downstream (outside in this case) of the depression 13 of the first processing surface 1. The opening is arranged especially preferably at a position opposite to the flat surface 16 located nearer to the outer diameter than a position where the direction of flow upon introduction by the micro-pump effect is changed to the direction of a spiral and laminar flow formed between the processing surfaces. Specifically, in FIG. 2(B), a distance n from the outermost side of the depression 13 arranged in the first processing surface 1 in the radial direction is preferably about 0.5 mm or more. Especially in the case of separating nanomicroparticles which is nano-sized particles from a fluid, it is preferable that mixing of a plurality of fluids to be processed and separation of the nano microparticles therefrom be effected under the condition of a laminar flow.

This second introduction part d2 may have directionality. For example, as shown in FIG. 3(A), the direction of introduction from the opening d20 of the second processing surface 2 is inclined at a predetermined elevation angle ($\theta 1$) relative to the second processing surface 2. The elevation angle ($\theta 1$) is set at more than 0° and less than 90°, and when the reaction speed is high, the angle ($\theta 1$) is preferably set in the range of 1° to 45°.

In addition, as shown in FIG. 3(B), introduction from the opening d20 of the second processing surface 2 has directionality in a plane along the second processing surface 2. The direction of introduction of this second fluid is in the outward direction departing from the center in a radial component of the processing surface and in the forward direction in a rotation component of the fluid between the rotating processing surfaces. In other words, a predetermined angle ($\theta 2$) exists facing the rotation direction R from a reference line g, which is the line to the outward direction and in the radial direction passing through the opening d20. This angle ($\theta 2$) is also set preferably at more than 0° and less than 90°.

This angle ($\theta 2$) can vary depending on various conditions such as the type of fluid, the reaction speed, viscosity, and the rotation speed of the processing surface. In addition, it is also possible not to give the directionality to the second introduction part d2 at all.

In the embodiment shown in FIG. 1, kinds of the fluid to be processed and numbers of the flow path thereof are set two respectively; but they may be one, or three or more. In the embodiment shown in FIG. 1, the second fluid is introduced into between the processing surfaces 1 and 2 from the introduction part d2; but this introduction part may be arranged in the first processing member 10 or in both. Alternatively, a plurality of introduction parts may be arranged relative to one fluid to be processed. The opening for introduction arranged in each processing member is not particularly restricted in its form, size, and number; and these may be changed as appropriate. The opening for introduction may be arranged just before the first and second processing surfaces 1 and 2 or in the side of further upstream thereof.

Meanwhile, because it is good enough only if the reaction could be effected between the processing surfaces 1 and 2, as opposed to the foregoing method, a method wherein the second fluid is introduced from the first introduction part d1 and a solution containing the first fluid is introduced from the second introduction part d2 may also be used. That is, the expression "first" or "second" for each fluid has a meaning for merely discriminating an $n^{th}$ fluid among a plurality of the fluids present; and therefore, a third or more fluids can also exist.

In the above-mentioned apparatus, a treatment such as separation/precipitation and crystallization is effected while the fluids are being mixed forcibly and uniformly between the processing surfaces 1 and 2 which are disposed in a position they are faced with each other so as to be able to approach to and separate from each other, at least one of which rotates relative to the other, as shown in FIG. 1. Particle diameter and monodispersity of the treated substance to be processed can be controlled by appropriately controlling rotation speed of the processing members 10 and 20, flow velocity, distance between the processing surfaces, concentration of raw materials in the fluids to be processed, kind of solvents in the fluids to be processed, and so forth.

Hereunder, specific embodiments as to the method for producing barium titanyl salt by using the above-mentioned apparatus will be explained.

In the apparatus shown above, the compound solution in which at least one compound is dissolved in a solvent (first fluid) and the barium-titanium mixed solution in which at least one kind each of the barium compound and the titanium compound are dissolved in a solvent (second fluid) are mixed in the thin film fluid formed between the processing surfaces which are disposed in a position they are faced with each other so as to be able to approach to and separate from each other, at least one of which rotates relative to the other, thereby separating the barium titanyl salt. On this occasion, at least any one of the first fluid and the second fluid shall contain an acidic substance.

The reaction to separate the barium titanyl salt takes place in the apparatus as shown in FIG. 1 of the present application while the fluids are being mixed forcibly and uniformly between the processing surfaces 1 and 2 which are disposed in a position they are faced with each other so as to be able to approach to and separate from each other, at least one of which rotates relative to the other.

At first, the compound solution is introduced as the first fluid from the first introduction part d1, which is one flow path, into between the processing surfaces 1 and 2 which are disposed in a position they are faced with each other so as to be able to approach to and separate from each other, at least one of which rotates relative to the other, thereby forming between the processing surfaces a first fluid film which is a thin film fluid formed of the first fluid.

Then, the barium-titanium mixed solution is introduced as the second fluid directly into the first fluid film formed between the processing surfaces 1 and 2 from the second introduction part d2 which is another flow path.

By so doing, the first fluid and the second fluid are mixed between the processing surfaces 1 and 2 while the distance therebetween is fixed by pressure balance between the supply pressure of the fluids to be processed and the pressure that is applied between the rotating processing surfaces, thereby effecting the reaction to separate the barium titanyl salt.

Meanwhile, because it is good enough only if the reaction could be effected between the processing surfaces 1 and 2, as opposed to the foregoing method, a method wherein the second fluid is introduced from the first introduction part d1 and a solution containing the first fluid is introduced from the second introduction part d2 may also be used. That is, the expression "first" or "second" for each fluid has a meaning for merely discriminating an $n^{th}$ fluid among a plurality of the fluids present; and therefore, a third or more fluids can also exist.

As discussed above, the processing apparatus may be provided with the third introduction part d3, in addition to the first introduction part d1 and the second introduction part d2; and in this case, from each introduction part, for example, the compound solution, the barium-titanium mixed solution, and the fluid which contains the acidic substance may be introduced into the processing apparatus separately as the first fluid, the second fluid, and the third fluid, respectively. In this case, the acidic substance may be contained at least in the third fluid, while may also be contained at least in any one of the first fluid and the second fluid or may not be contained in the first fluid nor in the second fluid. In other embodiment, the processing apparatus may be provided further with the fourth introduction part; and from each introduction part, for example, the compound solution, the barium solution in which a barium compound is dissolved in a solvent, the titanium solution in which a titanium compound is dissolved in a solvent, and a fluid which contains an acidic substance may be introduced into the processing apparatus separately as the first fluid, the second fluid, the third fluid, and the fourth fluid, respectively. In this case, the acidic substance may be contained at least in the fourth fluid, while may also be contained in at least anyone of the first to the third fluids or may not be contained in any of the first fluid, the second fluid, and the third fluid. By so doing, concentration and pressure of each solution can be controlled separately so that the separation reaction, stabilization of the particle diameter of the microparticles, and so on can be controlled more precisely. Meanwhile, a combination of the fluids to be processed (first to fourth fluids) that are introduced into the respective introduction parts may be set arbitrarily. The same is applied if the fifth or more introduction parts are arranged; and by so doing, fluids to be introduced into the processing apparatus may be subdivided.

In addition, temperatures of the fluids to be processed such as the first fluid, the second fluid, and so on may be controlled; and temperature difference among the first fluid, the second fluid, and so on (namely, temperature difference among each of the supplied fluids to be processed) may be controlled either. To control temperature and temperature difference of each of the supplied fluids to be processed, a mechanism with which temperature of each of the fluids to be processed is measured (temperature of the fluid before introduction to the processing apparatus, or in more detail, just before introduction into between the processing surfaces 1 and 2) so that each of the fluids to be processed that is introduced into between the processing surfaces 1 and 2 may be heated or cooled may be installed.

By carrying out the present invention, the barium titanyl salt having the ratio of the barium to the titanium controlled at about 1 can be produced more conveniently with lower energy and lower cost than ever; and in addition, there is no significant problem in particle diameter of the obtained particles. Accordingly, the present invention should not be understood in a limited way by the particle diameter of the obtained particles, wherein smaller particles than the distance between the processing surfaces 1 and 2 can be obtained; and thus, the particles may be nanoparticles with the average diameter of less than 1 μm, or the diameter thereof may be larger than it.

EXAMPLES

Hereinafter, the present invention will be explained in more detail by referring to Examples; but the present invention is not limited only to these Examples.

It is to be noted here that the term "from the center" in the following Examples means "from the first introduction part d1" of the processing apparatus shown in FIG. 1; the first fluid means the first fluid to be processed that is introduced through the first introduction part d1 of the processing apparatus as described before; and the second fluid means the second fluid to be processed that is introduced through the second introduction part d2 of the processing apparatus shown in FIG. 1, as described before.

Powder X-Ray Diffraction: XRD

The X-ray diffraction measurement was done by using the fully automated multi-purpose X-ray diffraction instrument X'Pert PRO MPD (manufactured by PANalytical B. V.). The diffraction strength was measured in the diffraction range of 10 to 100° as 2θ.

ICP Emission Spectroscopic Analysis

For the ICP emission spectrometric analysis, ICPS-8100 (sequential type, manufactured by Shimadzu Corp.) was used to measure concentrations of barium (Ba) and titanium (Ti) in the obtained microparticle powders.

Examples 1 to 6 and Comparative Examples 1 to 4

In Examples 1 to 6, the separation reaction is carried out by mixing a compound solution with a barium-titanium mixed solution in a thin film fluid formed between the processing surfaces 1 and 2 which are disposed in a position they are faced with each other so as to be able to approach to and separate from each other, at least one of which rotates relative to the other, in the apparatus as shown in FIG. 1, in which the fluids are uniformly dispersed, agitated, and mixed in the said thin film fluid.

While an aqueous oxalic acid solution was introduced, as the first fluid, from the center with the supply pressure of 0.50 MPa and the back pressure of 0.02 MPa and with the rotation speed of 1000 to 3000 rpm, a mixed solution of barium chloride dihydrate with titanium tetrachloride which was obtained by mixing an aqueous titanium tetrachloride with a solution obtained after dissolving barium chloride dihydrate in aqueous nitric acid was introduced as the barium-titanium mixed solution second solution) into between the processing surfaces 1 and 2 at the rate of 5 mL/minute. The first fluid and the second fluid were mixed in the thin film fluid to separate the barium titanyl oxalate microparticles; and the fluid thus obtained was discharged from the processing surfaces as the disperse solution of the barium titanyl oxalate microparticles.

To remove impurities from the discharged disperse solution of the barium titanyl oxalate microparticles, the barium titanyl oxalate microparticles were loosely aggregated; and thereafter, they were collected by filtration by using a filtering cloth having diameter of 1 μm and then washed by using pure water. The finally obtained paste of the barium titanyl oxalate microparticles was dried at 50° C. under vacuum of −0.1 MPaG. As to the obtained barium titanyl oxalate microparticle powders, XRD and ICP were measured.

In Comparative Examples 1 to 2 and 3 to 4, the above experiments were repeated by changing the solvent for dissolving barium chloride dehydrate to purified water. In Table 1, the processing conditions and ratio of the barium to the titanium in the barium titanyl oxalate obtained from the ICP measurement results are shown. Meanwhile, diameter of the primary particles in these Examples and Comparative Examples by the TEM observation was in the range of about 100 to about 500 nm.

Supply temperature of each of the first fluid and the second fluid shown in Table 1 were measured just before introduction of the first fluid and the second fluid into the processing apparatus respectively (in other words, just before introduction of the respective fluids into between the processing surfaces 1 and 2).

Figure 4:
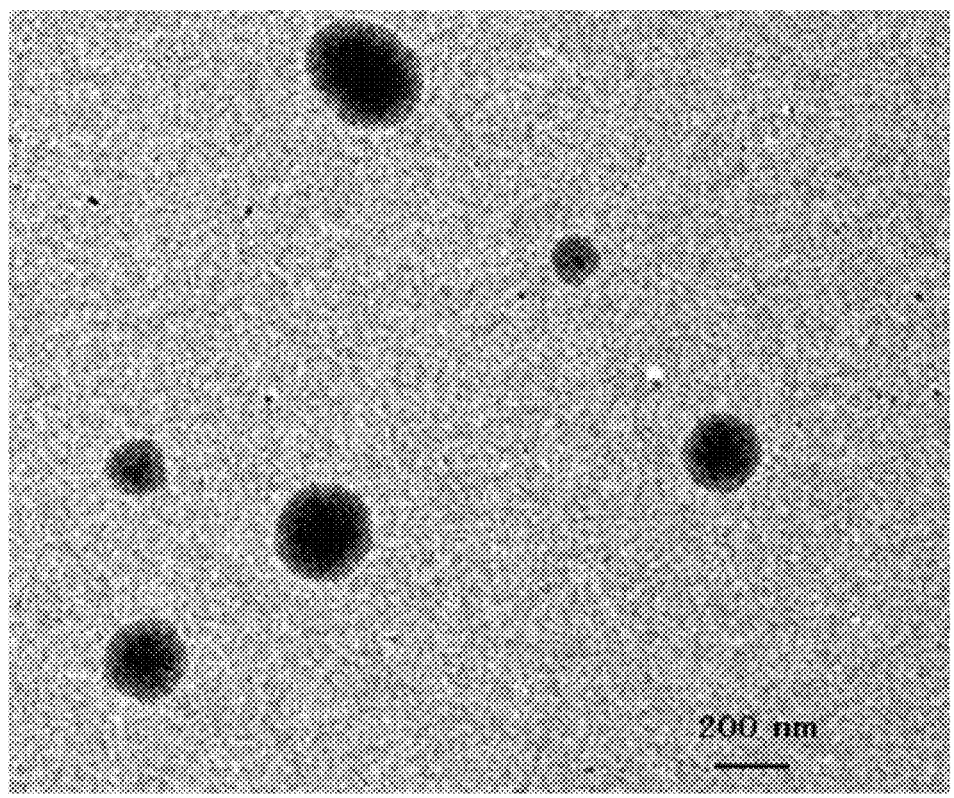
[FIG. 4]
FIG. 4 This shows the TEM picture of the barium titanyl oxalate obtained in Example 1 of the present invention.
Figure 5:
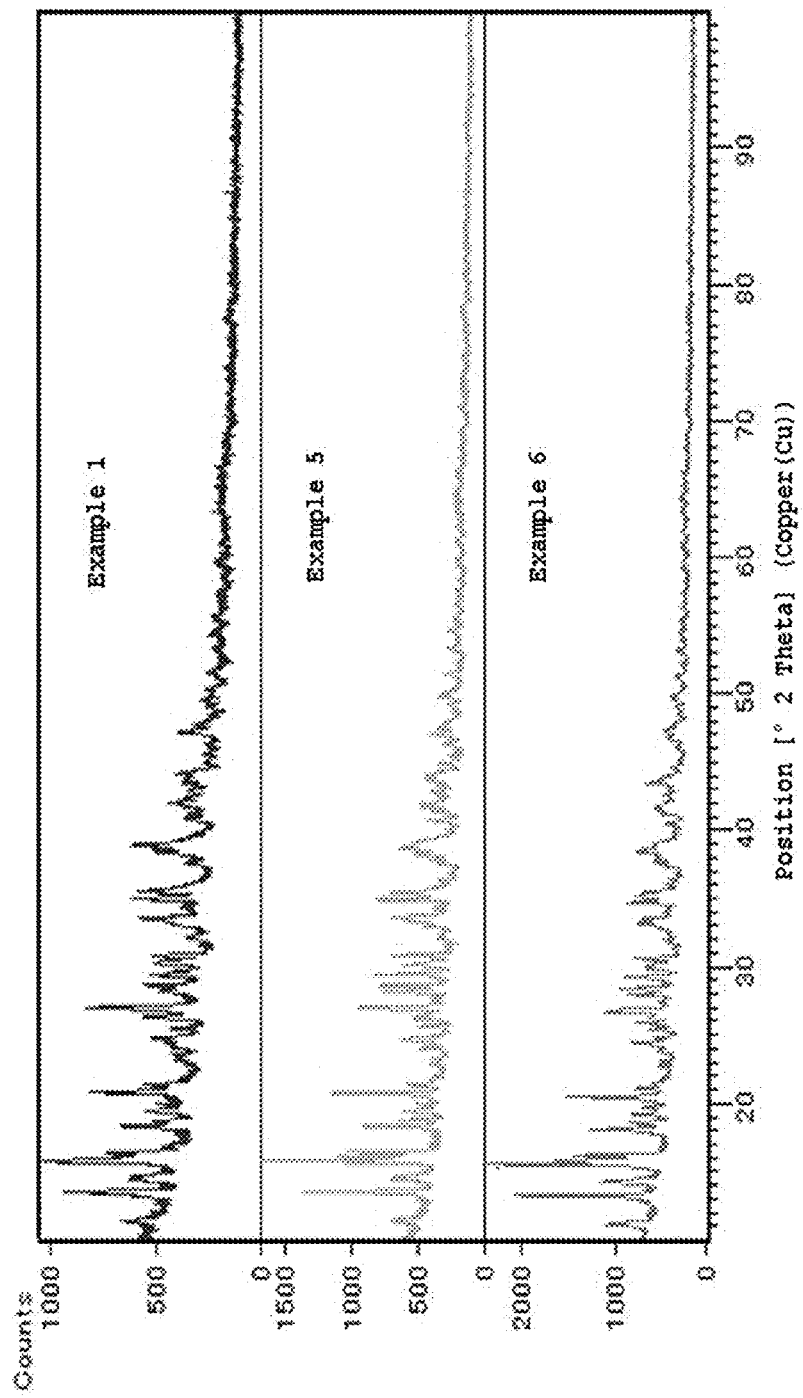
[FIG. 5]
FIG. 5 This is the XRD charts showing the XRD measurement results of the barium titanyl oxalates obtained in Example 1, 5, and 6 of the present invention.

The TEM picture of the barium titanyl oxalate microparticles obtained in Example 1 is shown in FIG. 4, and the XRD measurement results of the barium titanyl oxalate microparticles obtained in Examples 1, 5, and 6 are shown in FIG. 5.

From Table 1, it can be seen that when the reaction solution containing the barium titanyl salt microparticles which are separated by mixing the barium-titanium mixed solution with the compound solution was made to contain nitric acid, the ratio of the barium to the titanium in the obtained barium titanyl oxalate becomes about 1. From Table 1, the TEM picture, and the XRD measurement results, the barium titanyl oxalate obtained in these Examples was confirmed to be crystalline microparticles.

TABLE 1

| | | First fluid | | | Second fluid | | | |
|---|---|---|---|---|---|---|---|---|
| | | Kind | Supply temp. (°C.) | Supply rate (mL/minute) | Kind | Solvent to dissolve barium chloride dihydrate | Supply temp. (°C.) | Rotation number (rpm) | Ba/Ti (mol ratio) |
| Example | 1 | 5% by weight aq. oxalic acid solution | 20 | 100 | 6.5% by weight barium chloride dihydrate/5.0% by weight titanium tetrachloride mixed solution | 0.1N aq. nitric acid solution | 25 | 3000 | 0.99 |
| | 2 | | 20 | 100 | | | 25 | 1000 | 1.06 |
| | 3 | | 80 | 100 | | | 25 | 1000 | 0.93 |
| Comparative Example | 1 | | 20 | 100 | | Pure water | 25 | 3000 | 2.78 |
| | 2 | | 80 | 100 | | | 25 | 1000 | 3.67 |
| Example | 4 | 20% by weight aq. oxalic acid solution | 80 | 100 | 13.3% by weight barium chloride dihydrate/8.6% by weight titanium tetrachloride mixed solution | 0.2N aq. nitric acid solution | 25 | 1700 | 0.92 |
| | 5 | | 80 | 200 | | | 80 | 1700 | 1.01 |
| | 6 | | 80 | 300 | | | 50 | 1700 | 0.98 |
| Comparative Example | 3 | | 80 | 200 | | Pure water | 80 | 1700 | 0.82 |
| | 4 | | 80 | 300 | | | 50 | 1700 | 0.80 |

1 first processing surface
2 second processing surface
10 first processing member
11 first holder
20 second processing member
21 second holder
d1 first introduction part
d2 second introduction part
d20 opening

The invention claimed is:

1. A method for producing a barium titanyl salt: using at least two fluids as fluids to be processed,
of these fluids, at least one fluid is a barium-titanium mixed solution in which a barium compound and a titanium compound are dissolved in a solvent, and
at least one fluid other than the said fluid is a compound solution in which at least one compound to separate, as the barium titanyl salt, the barium and the titanium which are contained in the barium-titanium mixed solution is dissolved in a solvent, whereby
the said two or more of the fluids to be processed are mixed to separate the barium titanyl salt, wherein
at least one acidic substance is contained in at least any one of the barium-titanium mixed solution, the compound solution, and at least one solvent, which is a fluid to be processed, different from the barium-titanium mixed solution and the compound solution, wherein the at least one acidic substance excludes oxalic acid,
the said two, or three or more of the fluids to be processed are mixed in a thin film fluid formed between at least two processing surfaces which are disposed in a position they are faced with each other so as to be able to approach to and separate from each other, at least one of which rotates relative to the other,
thereby separating the barium titanyl salt;
wherein the compound is oxalic acid and/or a metal salt of oxalic acid, and the barium titanyl salt to be obtained is barium titanyl oxalate.

2. A method for producing a barium titanyl salt: using at least three fluids as fluids to be processed,
of these fluids, at least one fluid is a barium solution in which a barium compound is dissolved in a solvent,
at least one fluid other than the said fluid is a titanium solution in which a titanium compound is dissolved in a solvent, and
at least one fluid other than these fluids is a compound solution in which at least one compound is dissolved in a solvent, the said compound being to separate, as the barium titanyl salt, the barium which is contained in the barium solution and the titanium which is contained in the titanium solution, whereby
the said three or more fluids to be processed are mixed to separate the barium titanyl salt, wherein
at least one acidic substance is contained in at least any one of the barium solution, the titanium solution, the compound solution, and at least one solvent, which is a fluid to be processed, different from the barium solution, the titanium solution, and the compound solution, wherein the at least one acidic substance excludes oxalic acid,
the said three, or four or more of the fluids to be processed are mixed in a thin film fluid formed between at least two processing surfaces which are disposed in a position they are faced with each other so as to be able to approach to and separate from each other, at least one of which rotates relative to the other,
thereby separating the barium titanyl salt;
wherein the compound is oxalic acid and/or a metal salt of oxalic acid, and the barium titanyl salt to be obtained is barium titanyl oxalate.

3. The method for producing a barium titanyl salt according to claim 1, wherein the barium titanyl salt is crystalline.

4. A method for producing barium titanate, comprising:
producing barium titanyl salt by the method according to claim 1; and
synthesizing barium titanate by heat treating the barium titanyl salt.

5. The method for producing a barium titanyl salt according to claim 2, wherein the barium titanyl salt is crystalline.

6. A method for producing barium titanate, comprising:
producing barium titanyl salt by the method according to claim 2; and
synthesizing barium titanate by heat treating the barium titanyl salt.

7. A method for producing barium titanate, comprising:
producing barium titanyl salt by the method according to claim 3; and
synthesizing barium titanate by heat treating the barium titanyl salt.

8. The method for producing a barium titanyl salt according to claim 1, wherein the at least one acidic substance is selected from the group consisting of aqua regia, hydrochloric acid, nitric acid, fuming nitric acid, sulfuric acid, and fuming sulfuric acid.

9. The method for producing a barium titanyl salt according to claim 1, wherein the at least one acidic substance is nitric acid.

10. The method for producing a barium titanyl salt according to claim 2, wherein the at least one acidic substance is selected fro, the group consisting of aqua regia, hydrochloric acid, nitric acid, fuming nitric acid, sulfuric acid, and fuming sulfuric acid.

11. The method for producing a barium titanyl salt according to claim 2, wherein the at least one acidic substance is nitric acid.

* * * * *